(12) United States Patent
Zettler et al.

(10) Patent No.: US 9,333,055 B2
(45) Date of Patent: May 10, 2016

(54) ABUTMENT FOR A DENTAL IMPLANT

(75) Inventors: Marc Zettler, Rheinfelden/Baden (DE);
Hans Schürch, Titterten (CH)

(73) Assignee: STRAUMANN HOLDING AG, Basel (CH)

( * ) Notice: Subject to any disclaimer, the term of this patent is extended or adjusted under 35 U.S.C. 154(b) by 967 days.

(21) Appl. No.: 11/895,834

(22) Filed: Aug. 28, 2007

(65) Prior Publication Data
US 2008/0057476 A1 Mar. 6, 2008

(30) Foreign Application Priority Data

Aug. 29, 2006 (EP) ..................................... 06119671

(51) Int. Cl.
*A61C 8/00* (2006.01)

(52) U.S. Cl.
CPC ............... *A61C 8/005* (2013.01); *A61C 8/0066* (2013.01); *A61C 8/0054* (2013.01)

(58) Field of Classification Search
CPC ..... A61C 8/005; A61C 8/0066; A61C 8/0054
USPC .......................... 433/172, 173, 174, 175, 176
See application file for complete search history.

(56) References Cited

U.S. PATENT DOCUMENTS

| | | | |
|---|---|---|---|
| 5,674,069 A | 10/1997 | Osorio | |
| 5,810,592 A * | 9/1998 | Daftary | ......................... 433/173 |
| 2004/0101808 A1 | 5/2004 | Porter et al. | |
| 2004/0185420 A1* | 9/2004 | Schulter et al. | ............... 433/173 |
| 2006/0188846 A1* | 8/2006 | Wohrle et al. | ................. 433/173 |
| 2007/0202463 A1* | 8/2007 | Sanchez et al. | ............... 433/173 |

FOREIGN PATENT DOCUMENTS

| | | |
|---|---|---|
| DE | 195 34 979 C1 | 1/1997 |
| DE | 196 07 427 A1 | 3/1997 |
| EP | A-808-608 | 11/1997 |
| WO | WO 01/49199 A2 | 7/2001 |
| WO | WO 2006/102054 A1 * | 3/2006 ............... A61C 8/00 |

* cited by examiner

*Primary Examiner* — Ralph Lewis
(74) *Attorney, Agent, or Firm* — Scully Scott Murphy and Presser

(57) ABSTRACT

Abutment for a dental implant including an apical base portion equipped with profiled sections, a rotationally symmetrical transition portion bordering coronally on the base portion, a section bordering coronally on the transition portion and equipped with a wave-shaped rim, and an occlusal portion bordering coronally on the transition portion, the occlusal portion not being configured circular symmetric, a shoulder of irregular width is formed between the upper rim of section and the lower rim of the occlusal portion, the variation in width of the shoulder increasing from a minimum width to a maximum width by about 30% to 150% with respect to the minimum width of the shoulder.

9 Claims, 6 Drawing Sheets

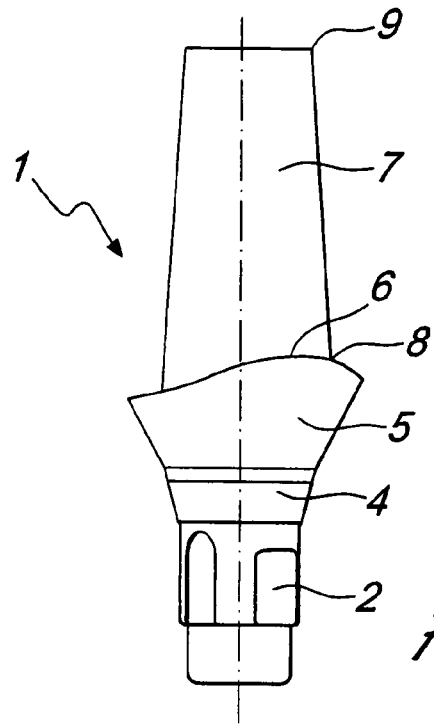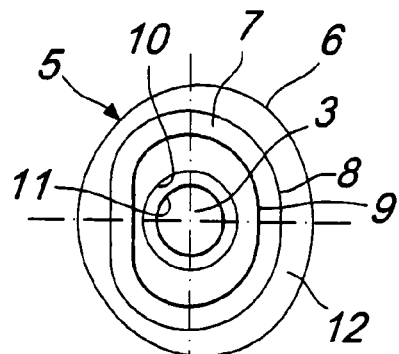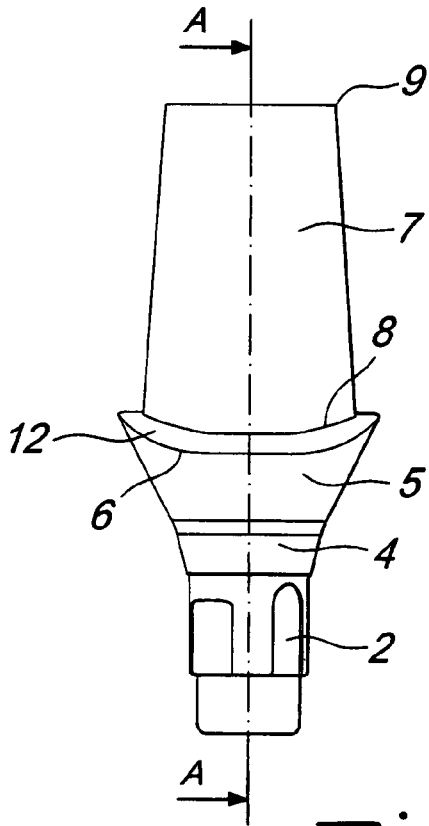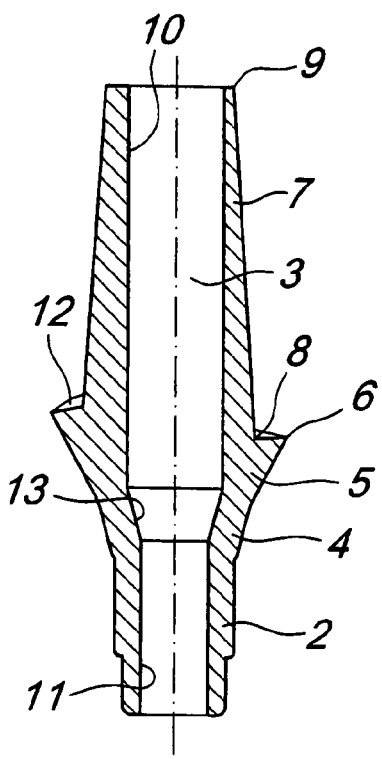

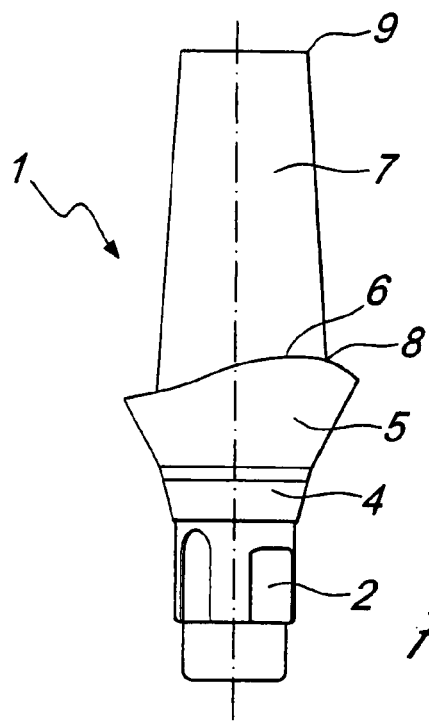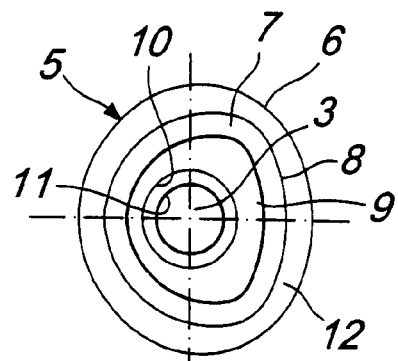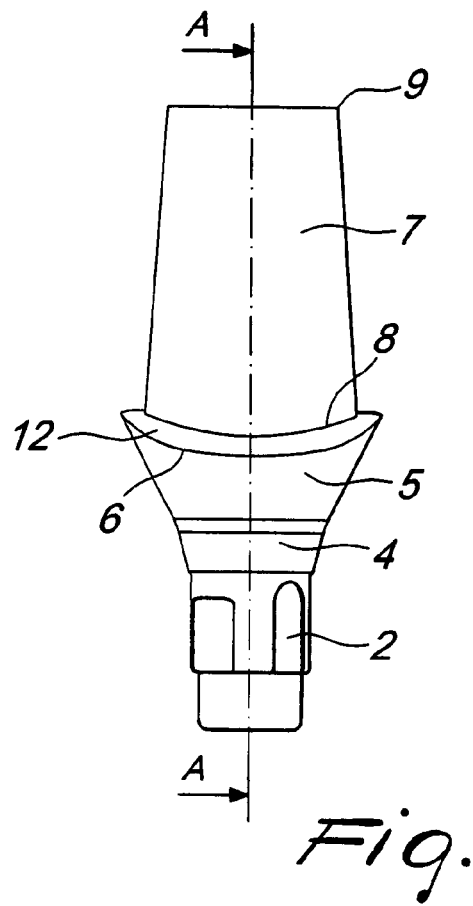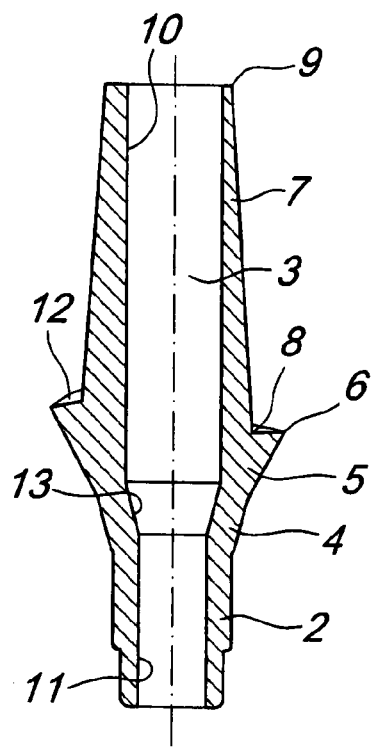
Fig. 3A
Fig. 3B
Fig. 3C
Fig. 3D

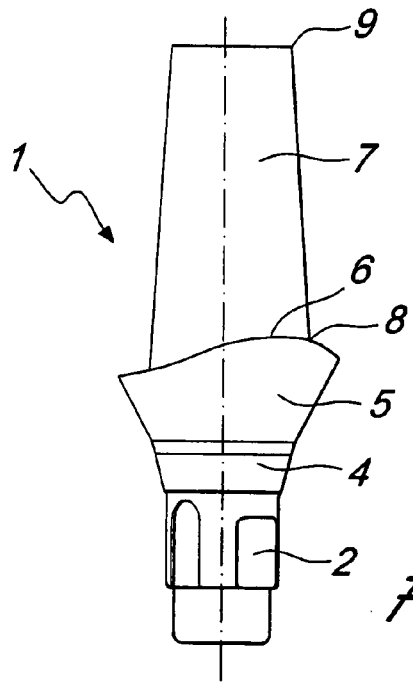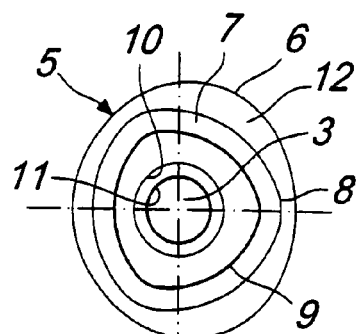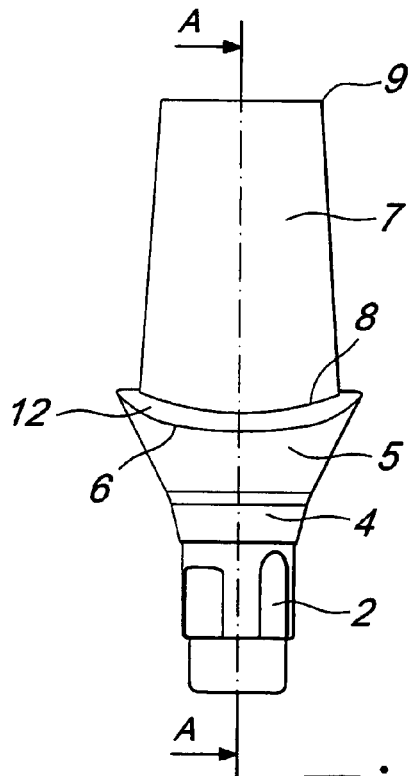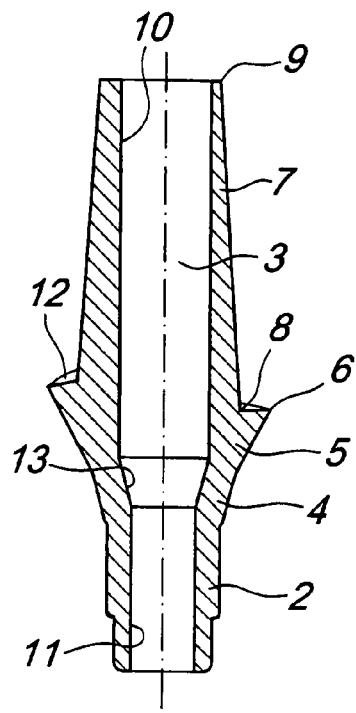
Fig. 4A
Fig. 4B
Fig. 4C
Fig. 4D

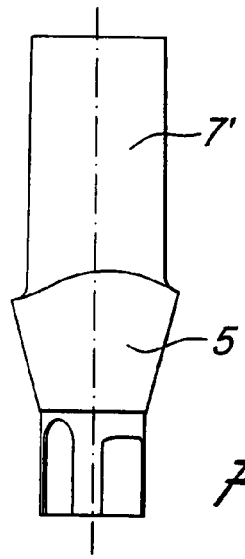
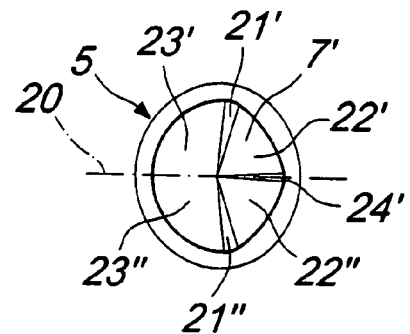
Fig. 6A  Fig. 6B
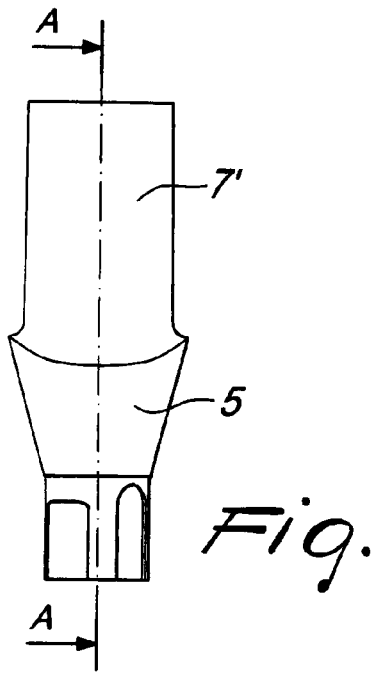
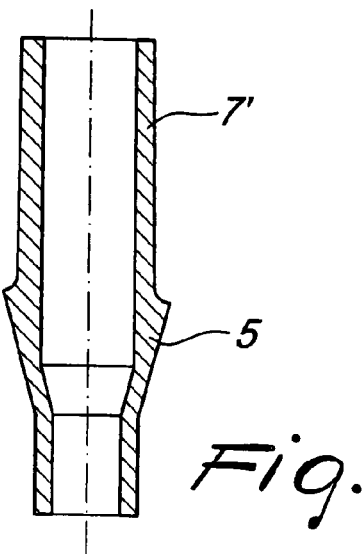
Fig. 6C  Fig. 6D
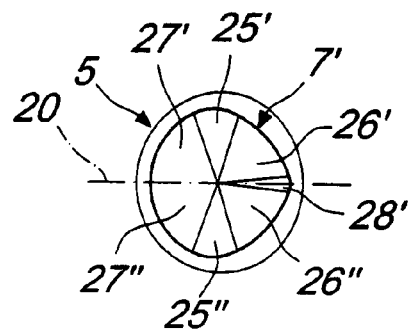
Fig. 6E

ABUTMENT FOR A DENTAL IMPLANT

The present invention refers generally to an abutment for a dental implant and specifically to an abutment for a dental implant with an improved occlusal portion.

BACKGROUND OF THE INVENTION

From US-A-5 674 069, there is known an abutment adapted for patients and having an occlusal asymmetrical truncated cone.

From EP-A-808 608, there is known an abutment for dental implants, an apical section of the abutment extending from the enossal portion of the dental implant being configured in the form of a symmetrical truncated cone bordering on a further coronal portion of the abutment which is configured asymmetrically; in particular, the latter portion of the abutment lingually has a parabolic base and labially a hemiellipsoidal base.

This asymmetry in EP-A-808 608 is supposed to ensure, as far as possible, an adaptation to the shape of the natural teeth within the oral cavity. In practice, however, it has been shown that this limitation to two base areas does not suffice for the complexity of shapes of the natural teeth.

In addition, EP-A-808 608 requires the provision of a shoulder of a regular width to be present between an occlusal truncated cone of the abutment and the rim of the differently shaped bases, which, with the small dimensions of the shoulder in the order of up to 0.1 mm, raises a problem in manufacturing the abutment.

SUMMARY OF THE INVENTION

Therefore, an object of the present invention is to provide an abutment for a dental implant which avoids the above-mentioned problems.

Within this aim, an object of the present invention is to devise an abutment for a dental implant which complies with a plurality of shapes of the natural teeth.

In addition, another object of the present invention is to provide an abutment for a dental implant which can be manufactured more easily, without the requirement for a shoulder of a regular width between an occlusal truncated cone of the abutment and the rim of the bases.

This aim and these and other objects which will appear more clearly in the following specification are solved by an abutment for a dental implant as set out in the appended claims.

BRIEF DESCRIPTION OF THE DRAWINGS

Further features and advantages of the present invention as well as the mode of use of the exemplary embodiments thereof are described hereinafter with reference to the accompanying drawings, wherein:

FIG. 2A shows an interdental or approximal view of an abutment according to a second embodiment of the invention;

FIG. 2B shows a top plan view of the abutment in FIG. 2A;

FIG. 2C shows a view of the labial side of the abutment in FIG. 2A;

FIG. 2D shows a sectional view taken along the line A-A in FIG. 2C;

FIG. 3A shows an interdental or approximal view of an abutment according to a third embodiment of the invention;

FIG. 3B shows a top plan view of the abutment in FIG. 3A;

FIG. 3C shows a view of the labial side of the abutment in FIG. 3A;

FIG. 3D shows a sectional view taken along the line A-A in FIG. 3C;

FIG. 4A shows an interdental or approximal view of an abutment according to a fourth embodiment of the invention;

FIG. 4B shows a top plan view of the abutment in FIG. 4A;

FIG. 4C shows a view of the labial side of the abutment in FIG. 4A;

FIG. 4D shows a sectional view taken along the line A-A in FIG. 4C;

FIG. 6A shows an interdental or approximal view of an abutment according to a sixth embodiment of the invention;

FIG. 6B shows a top plan view of the abutment in FIG. 6A;

FIG. 6C shows a view of the labial side of the abutment in FIG. 6A;

FIG. 6D shows a sectional view taken along the line A-A in FIG. 6C; and

FIG. 6E is a variation of the top plan view in FIG. 6B.

Figure 1A:
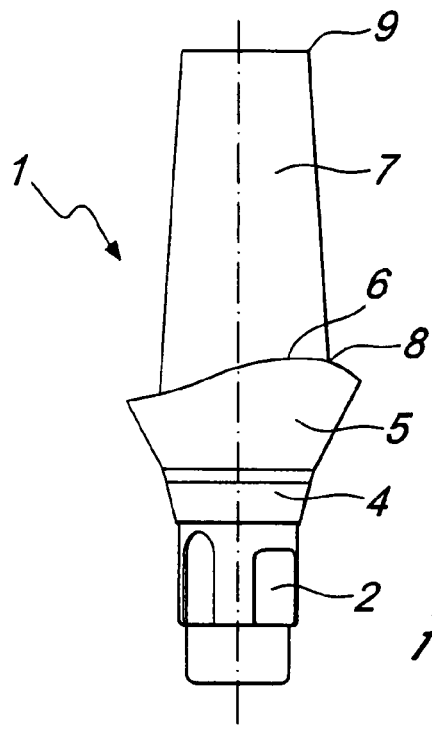
FIG. 1A shows an interdental or approximal view of an abutment according to a first embodiment of the invention.

The drawings illustrate the present invention and, in combination with the specification, are further used to explain the principles of the invention and to enable a person skilled in the art to manufacture and use the invention.

DESCRIPTION OF PREFERRED EMBODIMENTS

With reference to FIGS. 1A through 1D, a first embodiment of the abutment for a dental implant according to the present invention is described. The abutment, generally identified by reference number 1, is provided with a base portion 2 adapted to be accommodated in an implant (not shown). As is well-known to the person skilled in the art, the base portion 2 has profiled sections for securing the abutment 1 against rotation in the implant. In addition, the abutment 1 is provided, as is well-known in the art, with a through bore 3 adapted to accommodate a screw (also not shown) for securing the abutment to the implant.

The base portion 2 of the abutment 1 borders on a rotationally symmetrical transition portion 4 which is preferably configured as a truncated cone.

The transition portion 4 goes over to a section 5 having in its approximal view a wave-shaped upper rim 6, with a crest in the approximal region and soles in the lingual and labial section, respectively. As can be seen in FIG. 1A, the sole of the labial area lies slightly lower than the sole of the lingual area so that a morphology-dependent adaptation of the abutment is achieved.

Figure 1B:
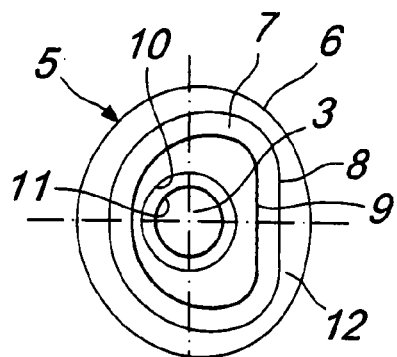
FIG. 1B shows a top plan view of the abutment in FIG. 1A.
Figure 1C:
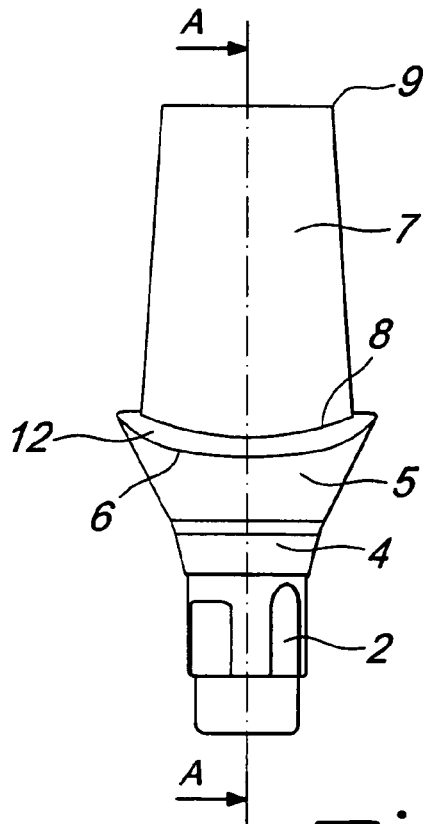
FIG. 1C shows a view of the labial side of the abutment in FIG. 1A.
Figure 1D:
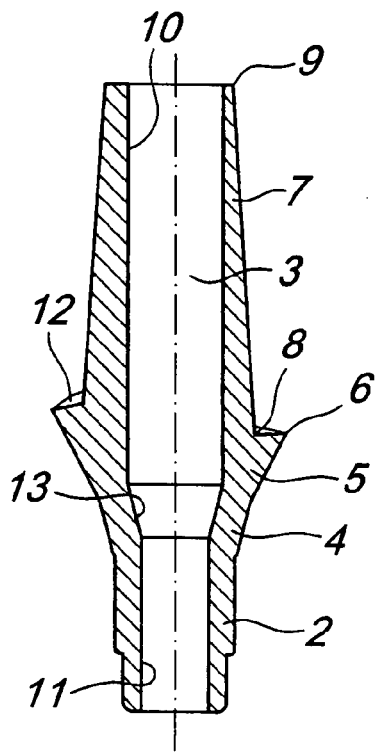
FIG. 1D shows a sectional view taken along the line A-A in FIG. 1C.
Figure 5A:
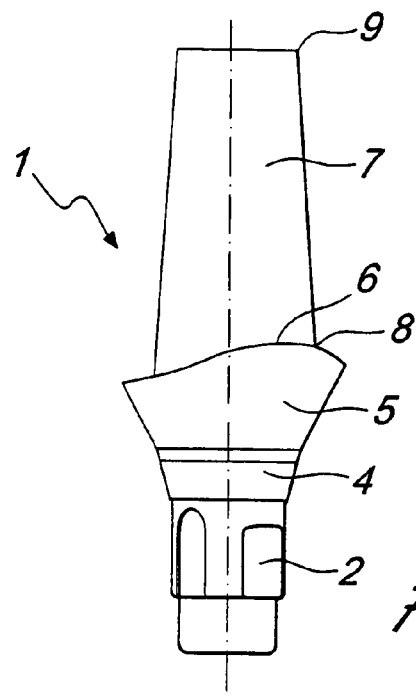
FIG. 5A shows an interdental or approximal view of an abutment according to a fifth embodiment of the invention.
Figure 5B:
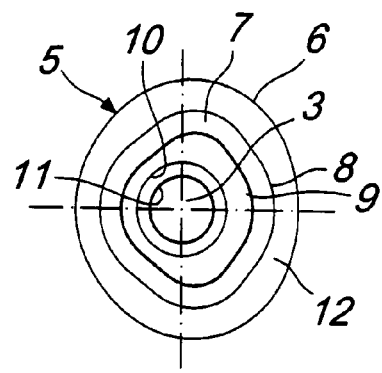
FIG. 5B shows a top plan view of the abutment in FIG. 5A.
Figure 5C:
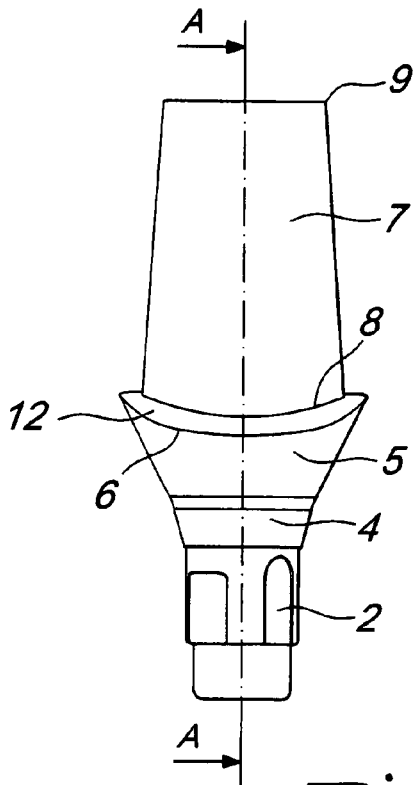
FIG. 5C shows a view of the labial side of the abutment in FIG. 5A.
Figure 5D:
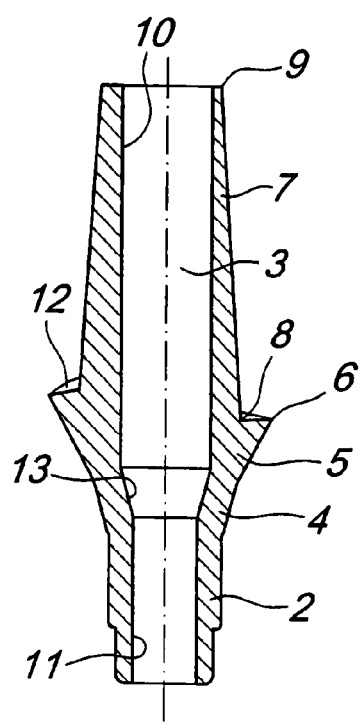
FIG. 5D shows a sectional view taken along the line A-A in FIG. 5C.

According to the invention, an occlusal portion 7 of the abutment 1, bordering on section 5, is non-circular symmetric, a shoulder 12 of irregular width being provided between the upper rim 6 of section 5 and a lower rim 8 of an occlusal portion 7, as can be seen in FIG. 1B. Thus, it is possible to configure the occlusal portion 7 with a cross-sectional geometry which differs from that of section 5 in order to achieve a better adaptation to the morphology of the mouth.

It has been surprisingly found that in spite of the irregular configuration of the shoulder 12, good results in integration and healing of the implant-based provision are achieved. In addition manufacturing of the abutment 1 with the non-circular symmetric occlusal portion 7 is facilitated since the regularity of the shoulder 12 is no longer necessary. In practice it has been shown that variations from about 20% to about 300% in the width of the shoulder 12, which are in the order of 0.1 to 1 mm, are acceptable. Therefore, according to the invention, the aforementioned range is comprised. In the first embodiment, for instance, the variation amounts to about 75%.

The occlusal portion 7 is configured in the form of a truncated cone, the lower rim 8 whereof being substantially parallel to the upper rim 9. According to the invention, the lingually positioned portion of the occlusal portion 7 is flat and, as shown in the top plan view of FIG. 1B, nearly rectilinear, whereas the labially positioned portion and the approximal portions of the occlusal portion 7 are rounded. Thus, according to the invention, a better adaptation to the morphology of the mouth can be achieved and, at the same time, it becomes possible to produce an abutment suitable for prefabrication in larger numbers.

In its occlusal portion 7, the through bore 3 has a portion 10 with a larger diameter than a portion 11 of the through bore 3 in the base portion 2, the through bore 3 having, in its transition portion 4, a portion 13 in the form of a truncated cone. This portion is used as a bearing area for the screw head when the abutment is fixed in the implant.

With reference to FIGS. 2A through 2D, a second embodiment of the abutment for a dental implant according to the present invention is described. In this second embodiment, same reference numbers as in the figures of the first embodiment are used to designate the same parts.

Differing from the first embodiment, the labially positioned portion of the occlusal portion 7 is flat and, as shown in the top plan view of FIG. 2B, nearly rectilinear, whereas the lingually positioned portion and the approximal portions of the occlusal portion 7 are rounded in order to achieve a morphology-dependent adaptation of the implant. In the second embodiment as well, the variation in width of the shoulder 12 amounts to about 75%.

With reference to FIGS. 3A through 3D, a third embodiment of the abutment for a dental implant according to the present invention is described. In this third embodiment, same reference numbers as in the figures of the first or second embodiment are used to designate the same parts.

Differing from the first embodiment, the occlusal portion 7 in the third one is substantially configured with a triangular cross-section, the vertices and the sides of the triangle being rounded. As can be seen in FIG. 3B, the lingually positioned portion of the occlusal portion 7 is formed by one side of the triangle so that this side, in a similar manner to the first embodiment, is flat. Instead, the labially positioned portion and the approximal portions of the occlusal portion 7 are rather rounded. In the third embodiment as well, the variation of the width of the shoulder 12 amounts to about 75%.

With reference to FIGS. 4A through 4D, a fourth embodiment of the abutment for a dental implant according to the present invention is described. In this fourth embodiment, same reference numbers as in the figures of the first, second or third embodiment are used to designate the same parts.

Differing from the third embodiment, the labially positioned portion of the occlusal portion 7 in the fourth one is flat and, as shown in the top plan view of FIG. 4B, nearly rectilinear, whereas the lingually positioned portion and the approximal portions of the occlusal portion 7 are rounded in order to achieve a morphology-dependent adaptation of the implant. In the fourth embodiment, the variation in width of the shoulder 12 amounts to about 150%.

With reference to FIGS. 5A through 5D, a fifth embodiment of the abutment for a dental implant according to the present invention is described. In this fifth embodiment, same reference numbers as in the figures of the first, second, third or fourth embodiment are used to designate the same parts.

Differing from the first embodiment, the occlusal portion 7 in the fifth one is substantially configured with a quadrangular cross-section, the angles and the sides of the quadrangle being rounded. In the fifth embodiment, the variation in width of the shoulder 12 amounts to about 30%.

With reference to FIGS. 6A through 6E, a sixth embodiment of the abutment for a dental implant according to the present invention is described. In this sixth embodiment, same reference numbers as in the figures of the first, second, third, fourth or fifth embodiment are used to designate the same parts.

Differing from the previous embodiments, the occlusal portion 7' is configured as a cylinder in the sixth embodiment. In addition, the cross-section of the cylinder, as can be seen from the diagrams in FIGS. 6B and 6E (the through hole having been omitted for simplification), consists of a plurality of circular arcs 21', 21", 22', 22", 23', 23" and 24'; or 25', 25", 26', 26", 27', 27" and 28', respectively, with different radii; each two circular arcs opposite to each other at the axis of symmetry 20 having identical radii.

In the sixth embodiment, the variation in width of the shoulder 12 amounts to about 45%.

The disclosures in EPA 06119671.3 from which this application claims priority are incorporated herein by reference.

What is claimed is:

1. A one-piece abutment for a dental implant, comprising:
    an apical base portion provided with sections for securing the abutment against rotation in the implant,
    a rotationally symmetrical transition portion bordering coronally on the base portion,
    a section bordering coronally on the transition portion and being provided with a wave-shaped rim,
    an occlusal portion bordering coronally on the transition portion, the occlusal portion being non-circular symmetric over the entire length thereof, and
    a shoulder having an irregular width between an upper rim of said section and a lower rim of the occlusal portion, wherein a change in width of the shoulder between a maximum width of the shoulder and a minimum width of the shoulder is about 30% to about 150% of said minimum width,
    wherein the occlusal portion is configured as a truncated cone.

2. The abutment according to claim 1, wherein the change in the width is about 30% to about 75% of the minimum width.

3. The abutment according to claim 1, wherein the change in the width is about 45% to about 75% of the minimum width.

4. The abutment according to claim 1, wherein the occlusal portion is configured as a cylinder.

5. The abutment according to claim 4, wherein the cross-section of the cylinder is formed from a multiplicity of circular arcs with different radii, each two said circular arcs opposite each other having identical radii.

6. The abutment according to claim 1, wherein the transition portion is configured as a rotationally symmetrical truncated cone.

7. The abutment according to claim 1, wherein the upper rim of said section is configured wave-shaped, with a crest in the approximal region and soles in a lingual and a labial section, respectively.

8. The abutment according to claim 7, wherein the sole of the lingual portion is positioned slightly higher than the sole of the labial portion.

9. The abutment according to claim 1, wherein said shoulder has a coronal planar surface configuration.

\* \* \* \* \*